United States Patent
Kanikanti et al.

(10) Patent No.: US 7,763,583 B2
(45) Date of Patent: Jul. 27, 2010

(54) ENDOPARASITICIDAL COMPOSITIONS FOR TOPICAL APPLICATION

(75) Inventors: Venkata-Rangarao Kanikanti, Leverkusen (DE); Thomas Bach, Wuppertal (DE); Gertraut Altreuther, Wuppertal (DE); Michael Traeubel, Cologne (DE); Hans-Juergen Hamann, Dormagen (DE)

(73) Assignee: Bayer Animal Health GmbH (DE)

( * ) Notice: Subject to any disclaimer, the term of this patent is extended or adjusted under 35 U.S.C. 154(b) by 0 days.

(21) Appl. No.: 11/451,676

(22) Filed: Jun. 13, 2006

(65) Prior Publication Data

US 2007/0060509 A1 Mar. 15, 2007

Related U.S. Application Data

(63) Continuation of application No. PCT/EP2004/013552, filed on Nov. 30, 2004.

(51) Int. Cl.
  *A61K 38/12* (2006.01)
(52) U.S. Cl. .......................................... 514/9
(58) Field of Classification Search ........................ None
  See application file for complete search history.

(56) References Cited

U.S. PATENT DOCUMENTS

| | | | |
|---|---|---|---|
| 4,001,411 A | | 1/1977 | Seubert et al. |
| 4,988,696 A | * | 1/1991 | Andrews et al. ............ 514/250 |
| 5,837,289 A | * | 11/1998 | Grasela et al. ............. 424/484 |
| 5,874,479 A | * | 2/1999 | Martin ...................... 514/724 |
| 6,159,932 A | * | 12/2000 | Mencke et al. ................ 514/9 |
| 6,340,672 B1 | | 1/2002 | Mihalik |
| 2002/0081292 A1 | | 6/2002 | Jancys |
| 2003/0125244 A1 | * | 7/2003 | Kalbe et al. .................... 514/9 |
| 2004/0198676 A1 | * | 10/2004 | Soll et al. ..................... 514/28 |

FOREIGN PATENT DOCUMENTS

| | | |
|---|---|---|
| CA | 2373827 A1 | 11/2000 |
| DE | 3619030 A1 | 12/1987 |
| EP | 0267404 | 5/1988 |
| EP | 0382173 | 8/1990 |
| EP | 0626375 | 11/1994 |
| EP | 0626376 | 11/1994 |
| EP | 0644883 | 3/1995 |
| EP | 0662326 | 7/1995 |
| EP | 1308163 | 5/2003 |
| WO | 9523590 | 9/1995 |
| WO | 9725976 | 7/1997 |
| WO | 9803157 | 1/1998 |
| WO | 9838165 | 9/1998 |
| WO | PCT/EP01/01392 | * 2/2001 |
| WO | 0115547 | 3/2001 |
| WO | 0160380 | 8/2001 |
| WO | 0162268 | 8/2001 |
| WO | 02094288 | 11/2002 |

OTHER PUBLICATIONS

M.A. Yamane et al. Int. J. Pharm. (1995) 116, pp. 237-251.*
Sinha, et al., "Permeation Enhancers for Transdermal Drug Delivery", Drug Development and Industrial Pharmacy, 26(11): p. 1131-1140 (2000).
Clarys, et al., "In vitro Percutaneous Penetration through Hairless Rat Skin: Influence of Temperature, Vehicle and Penetration Enhancers", Euro. J. of Pharma. and Biopharma., 46: p. 279-283 (1998).
Cevc, et al., "The Skin: A Pathway for Systemic Treatment with Patches and Lipid-based Agent Carriers", Advanced Drug Delivery Reviews, 18: p. 349-378 (1996).
Bauer, et al., Pharmazeutische Technologie, Thieme Verlag p. 364-367 (1993).
Gurny, et al., Dermal and Transdermal Drug Delivery, Wissenschaftliche Verlagsgesellschaft p. 131 (1993).
Magnusson B M et al., "Veterinary Drug Delivery: Potential for Skin Penetration Enhancement," Advanced Drug Delivery Reviews, Sep. 1, 2001, vol. 50, No. 3, pp. 205-227.

* cited by examiner

*Primary Examiner*—Andrew D Kosar

(57) ABSTRACT

The present invention relates to transdermally applicable compositions comprising cyclic depsipeptides and/or praziquantel, and to their preparation and their use for controlling endoparasites.

5 Claims, No Drawings

ENDOPARASITICIDAL COMPOSITIONS FOR TOPICAL APPLICATION

The present invention relates to transdermally applicable compositions comprising cyclic depsipeptides and/or praziquantel, and to their preparation and their use for controlling endoparasites.

The anthelmintically active compound praziquantel (U.S. Pat. No. 4,001,411) is usually administered orally, see, for example, DE-A-199 41 024, WO 98/03157, U.S. 2002/0081292 Al and WO 97/25976. In the case of topical application of endoparasiticides, the active compound has to pass into the bloodstream through the skin in order to reach the endoparasites in question. Since praziquantel is not particularly suitable for transdermal application, the topical transdermal application form is, owing to the difficulties to be expected, in particular in the case of dogs, uncommon for this active compound. A composition for the dermal treatment of helmintic diseases using praziquantel is described in EP-A-267 404. However, the application of this composition is limited to cats where effective transdermal application is generally considerably easier to achieve than, for example, in the case of dogs.

WO 01/60380 (Phoenix Scientific, Inc.) discloses parasiticidal formulations for injection or for pour-on application, which formulations may comprise a pyrrolidone solvent, a further solvent and a parasiticidally active compound. The extensive list of active compounds mentions, inter alia, praziquantel.

EP-A-1 308 163 (Wyeth) discloses endoparasiticidal-compositions in the form of gels comprising moxidectin, praziquantel, benzyl alcohol, ethanol, colloidal silica, a surfactant and an oil.

WO 95/23590 (Bomac Laboratories) discloses a complicated process for preparing anthelmintic compositions for dermal application. The compositions comprise a carrier, an emulsifier, an oil and a diluent. Suitable active compounds are especially benzimidazoles, but macrocyclic lactones and praziquantel are also mentioned, inter alia.

WO 02/094288 describes a veterinary pharmaceutical which comprises an avermectin oxime derivative, in particular selamectin, in combination with praziquantel. Proposed routes of administration include topical application; corresponding formulations comprise a di($C_{2-4}$-glycol) mono ($C_{1-4}$-alkyl) ether and, if appropriate, a skin-friendly solvent.

A cyclic depsipeptide PF 1022 and its action against endoparasites is known from EP-A 382 173.

Further cyclic depsipeptides and their endoparasiticidal action are subject-matter of the German patent applications EP-A 626 376; EP-A 626 375; EP-A 644 883.

Endoparasiticidal compositions comprising praziquantel or epsiprantel and cyclic depsipeptides are described in EP 662 326.

WO 96/38165 provides endoparasiticidal compositions comprising avermectins, ivernectins, milbemycins in combination with cyclic depsipeptides and also, if appropriate, praziquantel or epsiprantel.

Transdermally applicable compositions comprising cyclic depsipeptides for controlling endoparasites are described in WO 01/62268.

Permeation or penetration enhancers which improve the transdermal application of pharmaceuticals are known in principle from the prior art, see, for example, Sinha et al. in *Drug Development and Industrial Pharmacy*, 26(11), 1131-1140 (2000); Clarys et al. *European Journal of Pharmaceutics and Biopharmaceutics* 46 (1998), 279-283 and chapter 6 of Dermatopharmazie (Wissenschaftliche Verlagsgesellschaft mbH Stuttgart 2001).

However, the level of activity and/or duration of action of the compositions of the prior art is, in particular in the case of certain hosts, against certain organisms and/or at low application concentrations, not entirely satisfactory in all areas of use.

Because of the wide variety of requirements to be met by modem pharmaceuticals, for example concerning level of activity (for example plasma concentration of the active compound), duration of action, spectrum of action, range of applications, toxicity, combination with other active compounds, combination with formulation auxiliaries, and because of the possible occurrence of resistance, the development of novel pharmaceuticals cannot ever be regarded as complete, and there is a continuing great need for novel compositions which have advantages, at least in some aspects, over known compositions.

To enable the pet owner to apply endoparasiticidally active compounds in a manner which is as simple as possible, it is desirable to provide a transdermally applicable composition.

As is known from the literature, it is extremely difficult for molecules having molecular weights >1000 u to penetrate the skin when applied topically. Particularly poor is the penetration of peptides or proteins having relatively large molecular weights (Cevc et al., Advanced Drug Delivery Reviews 18 (1996) 349-378; Bauer et al. Pharmazeutische Technologie, 1993, p. 364, Thieme Verlag; Gurny et al. Dermal and Transdermal Drug Delivery, 1993, p. 131, Wissenschaftliche Verlagsgesellschaft). However, in the case of endoparasiticidally active compounds, penetration is a precondition, since the active compounds are intended to act against endoparasites, for example in the gastrointestinal tract.

Although a few publications of the prior art propose the topical application of praziquantel and/or cyclic depsipeptides, it is known to the person skilled in the art that these active compounds are not particularly suitable for this purpose and that, as a consequence, the known formulations are not entirely satisfactory, in particular in the case of, for example, so-called dose-driving worms, such as the whipworm *Trichuris vulpis* and/or the tapeworm *Taenia canis*.

Accordingly, it was an object of the present invention to provide a topically applicable endoparasiticidal composition having the following properties:

good transdermal action in various hosts, in particular dogs, also in the case of dose-driving worms (for example *Trichuris vulpis, Taenia canis*)
good skin-friendliness
long-term stability
user friendliness The present invention provides:
Compositions comprising:
as active compound a cyclic depsipeptide and/or praziquantel
a pyrrolidone solvent
a terpene penetration enhancer and/or an aliphatic fatty acid acting as penetration enhancer and/or an aliphatic fatty alcohol acting as penetration enhancer.

The present invention furthermore provides the preparation of the compositions mentioned above and their use for controlling endoparasites.

Depsipeptides are similar to peptides and differ from the latter in that one or more α-amino acid building blocks are replaced by α-hydroxycarboxylic acid building blocks. Preferred cyclic depsipeptides are those having 18 to 24 ring atoms, in particular 24 ring atoms.

The depsipeptides having 18 ring atoms include compounds of the general formula (I):

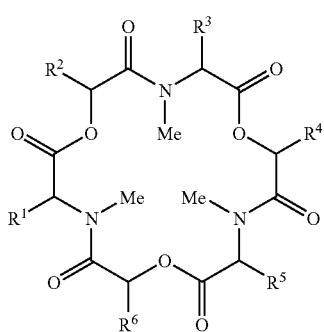

in which
R¹, R³ and R⁵ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, amninoalkyl, alkylaminoalkyl, dialkylaminoalkyl, guanidinoalkyl which may optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl and also optionally substituted arylalkyl, substituents which may be mentioned being halogen, hydroxyl, alkyl and alkoxy, R², R⁴ and R⁶ independently of one another represent hydrogen, straight-chain or branched alkyl having up to 8 carbon atoms, hydroxyalkyl, mercaptoalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoaklyl, alkenyl, cycloalkyl, cycloalkylalkyl, optionally substituted aryl or arylalkyl, substituents which may be mentioned being halogen, hydroxyl, alkyl, alkoxy, and their optical isomers and racemates.

Preference is given to compounds of the formula (I)

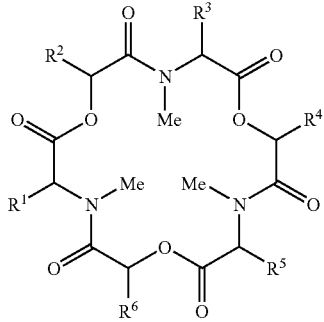

in which
R¹, R³ and R⁵ independently of one another represent straight-chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, mercapto-$C_1$-$C_6$-alkyl, in particular mercaptomethyl, $C_1$-$C_4$-alkylthio-$C_1$-$C_6$-alkyl, in particular methylthioethyl, $C_1$-$C_4$-alkylsulphinyl-$C_1$-$C_6$-alkyl, in particular methylsulphinylethyl, $C_1$-$C_4$-alkylsulphonyl-$C_1$-$C_6$-alkyl, in particular methylsulphonylethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-arylalkoxycarbonyl-$C_1$-$C_6$-alkyl, in particular benzyloxycarbonylmethyl, carbamoyl-$C_1$-$C_6$-alkyl, in particular carbamoylmethyl, carbamoylethyl, amino-$C_1$-$C_6$-alkyl, in particular aminopropyl, aminobutyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, guanidino-$C_1$-$C_6$-alkyl, in particular guanidinopropyl, $C_1$-$C_4$-alkoxycarbonylamino-$C_1$-$C_6$-alkyl, in particular tert-butoxycarbonylaminopropyl, tert-butoxycarbonylaminobutyl, 9-fluorenylmethoxycarbonyl(Fmoc)amino-$C_1$-$C_6$-alkyl, in particular 9-fluorenylmethoxycarbonyl(Fmoc)aminopropyl, 9-fluorenylmethoxycarbonyl(Fmoc)aminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl-$C_1$-$C_4$-alkyl, in particular phenylmethyl which may optionally be substituted by radicals from the group consisting of halogen, in particular fluorine, chlorine, bromine or iodine, hydroxyl, $C_1$-$C_4$-alkoxy, in particular methoxy or ethoxy, $C_1$-$C_4$-alkyl, in particular methyl, R², R⁴ and R⁶ independently of one another represent straight chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, mercapto-$C_1$-$C_6$-alkyl, in particular mercaptomethyl, $C_1$-$C_4$-alkylthio-$C_1$-$C_6$-alkyl, in particular methylthioethyl, $C_1$-$C_4$-alkylsulphinyl-$C_1$-$C_6$-alkyl, in particular methylsulphinylethyl, $C_1$-$C_4$-alkylsulphonyl-$C_1$-$C_6$-alkyl, in particular methylsulphonylethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-arylalkoxycarbonyl-$C_1$-$C_6$-alkyl, in particular benzyloxycarbonylmethyl, carbamoyl-$C_1$-$C_6$-alkyl, in particular carbamoylmethyl, carbamoylethyl, amino-$C_1$-$C_6$-alkyl, in particular aminopropyl, aminobutyl, $C_1$-$C_4$-alkylamino-$C_1$-$C_6$-alkyl, in particular methylaminopropyl, methylaminobutyl, $C_1$-$C_4$-alkylamino-$C_1$-$C_6$-alkyl, in particular dimethylaminopropyl, dimethylaminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl, phenyl-$C_1$-$C_4$-alkyl, in particular phenylmethyl which may optionally be substituted by radicals from the group consisting of halogen, in particular fluorine, chlorine, bromine or iodine, hydroxyl, $C_1$-$C_4$-alkoxy, in particular methoxy or ethoxy, $C_1$-$C_4$-alkyl, in particular methyl, and their optical isomers and racemates.

Particular preference is given to compounds of the formula (I), in which $R^1$, $R^3$ and $R^5$ independently of one another represent straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, $C_1$-$C_4$-alkoxycarbonylamino-$C_1$-$C_6$-alkyl, in particular tert-butoxycarbonylaminopropyl, tert-butoxycarbonylaminobutyl, $C_2$-$C_8$-alkenyl, in particular vinyl, allyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl-$C_1$-$C_4$-alkyl, in particular phenylmethyl which may optionally be substituted by one or more identical or different radicals of those mentioned above, $R^2$, $R^4$ and $R^6$ independently of one another represent straight-chain or branched $C_1$-$C_8$-alkyl, in particular methyl, ethyl, propyl, isopropyl, butyl, isobutyl, sec-butyl, tert-butyl, pentyl isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, aryl-$C_1$-$C_4$-alkyloxy-$C_1$-$C_6$-alkyl, in particular benzyloxymethyl, 1-benzyloxyethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-aryl-alkoxycarbonyl-$C_1$-$C_6$-alkyl, in particular benzyloxycarbonylmethyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl, phenyl-$C_1$-$C_4$-alkyl, in particular phenylmethyl which may optionally be substituted by one or more identical or different radicals of those mentioned above, and their optical isomers and racemates.

Very particular preference is given to compounds of the formula (I), in which $R^1$, $R^3$ and $R^5$ independently of one another represent straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular allyl, $C_3$-$C_7$-Cycloalkyl-$C_1$-$C_4$-alkyl, in particular cyclohexylmethyl, phenyl-$C_1$-$C_4$-alkyl, in particular phenylmethyl, $R^2$, $R^4$ and $R^6$ independently of one another represent straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular vinyl, allyl, $C_3$-$C_7$-cycloalkyl-$C_1$-$C_4$-alkyl, in particular cyclohexylmethyl, phenyl-$C_1$-$C_4$-alkyl, in particular phenylmethyl which may optionally be substituted by one or more identical or different radicals of those mentioned above, and their optical isomers and racemates.

In the sense of the above invention, it is possible to use all compounds of the general formula (I), which compounds may be present in optically active, stereoisomeric forms or as racemic mixtures. However, preference is given to using, according to the invention, the optically active stereoisomeric forms of the compounds of the general formula (I).

Specifically, the following compounds of the general formula (I) may be mentioned, where the radicals $R^1$ to $R^6$ are as defined below:

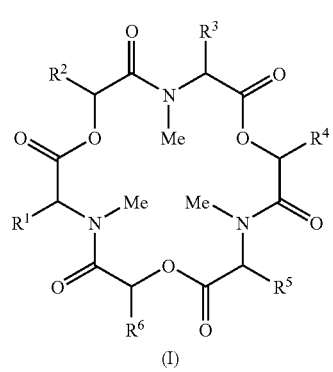

(I)

| $R^1$ | $R^2$ | $R^3$ | $R^4$ | $R^5$ | $R^6$ |
|---|---|---|---|---|---|
| —CHMeCH$_2$Me | -cyclohexyl | —CHMeCH$_2$Me | -Me | —CHMeCH$_2$Me | -Me |
| —CHMeCH$_2$Me | -cyclohexyl | —CHMeCH$_2$Me | -Me | —CHMeCH$_2$Me | -cyclohexyl |
| —CHMeCH$_2$Me | —CH$_2$-Phe | —CHMeCH$_2$Me | -Me | —CHMeCH$_2$Me | -Me |
| —CHMeCH$_2$Me | —CH$_2$-Phe | —CHMeCH$_2$Me | -Me | —CHMeCH$_2$Me | —CH$_2$-Phe |
| —CHMeCH$_2$Me | —(CH$_2$)$_3$-Me | —CHMeCH$_2$Me | -Me | —CHMeCH$_2$Me | -Me |
| —CHMeCH$_2$Me | —(CH$_2$)$_3$-Me | —CHMeCH$_2$Me | -Me | —CHMeCH$_2$Me | —(CH$_2$)$_3$-Me |
| —CHMe$_2$ | —CH$_2$-Phe | —CHMeCH$_2$Me | -Me | —CHMeCH$_2$Me | -Me |
| —CH$_2$-Phe | —CHMe$_2$ | —CH$_2$-Phe | —CHMe$_2$ | —CHMeCH$_2$Me | —CHMe$_2$ |

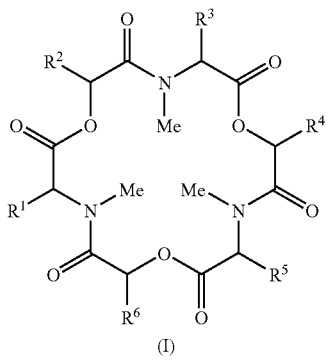

(I)

| R¹ | R² | R³ | R⁴ | R⁵ | R⁶ |
|---|---|---|---|---|---|
| —CH₂CHMe₂ | —CH₂-Phe | —CH₂CHMe₂ | -Me | —CH₂CHMe₂ | —CH₂-Phe |
| —(CH₂)₃-Me | -Me | —CHMeCH₂Me | -Me | —CHMeCH₂Me | -Me |
| —CHMe₂ | -Me | —CHMe₂ | -Me | —CHMe₂ | -Me |
| —CH₂-Me | -Me | —CH₂-Me | -Me | —CH₂-Me | -Me |
| —(CH₂)₂-Me | -Me | —(CH₂)₂-Me | -Me | —(CH₂)₂-Me | -Me |
| —(CH₂)₃-Me | -Me | —(CH₂)₃-Me | -Me | —(CH₂)₃-Me | -Me |
| —CH₂—CH=CH₂ | -Me | —CH₂—CH=C₂ | -Me | —(CH₂)—CH=CH₂ | -Me |
| —CHMeCH₂Me | -Me | —CHMeCH₂Me | -Me | —CHMeCH₂Me | —CH₂-Me |
| —CHMeCH₂Me | -Me | —CHMeCH₂Me | -Me | —CHMeCH₂Me | —(CH₂)₂-Me |
| —CHMeCH₂Me | -Me | —CHMeCH₂Me | -Me | —CHMeCH₂Me | —(CH₂)₃-Me |
| —CHMeCH₂Me | -Me | —CHMeCH₂Me | -Me | —CH₂Me | -Me |
| —CHMeCH₂Me | -Me | —CHMeCH₂Me | -Me | —(CH₂)₂-Me | -Me |
| -cyclohexyl | -Me | -cyclohexyl | -Me | -cyclohexyl | -Me |
| —CH₂CHMe₂ | -cyclohexyl | —CH₂CHMe₂ | -Me | —CH₂CHMe₂ | -cyclohexyl |
| —CH₂CHMe₂ | -cyclohexyl | —CH₂CHMe₂ | -Me | —CH₂CHMe₂ | -Me |
| —CHMeCH₂Me | —CHMe₂ | —CHMeCH₂Me | —CHMe₂ | —CHMeCH₂Me | -Me |
| —CH₂-Phe | -Me | —CH₂-Phe | -Me | —CH₂-Phe | -Me |
| -cyclohexyl | -Me | -cyclohexyl | -Me | -cyclohexyl | -Me |
| —CHMe₂ | —CHMe₂ | —CHMe | -Me | —CHMe₂ | -Me |
| —CHMe₂ | —CHMe₂ | —CHMe₂ | —CHMe₂ | —CHMe₂ | -Me |
| —CH₂-Me | —CHMe₂ | —CHMe₂ | -Me | —CH₂-Me | -Me |
| —CH₂-Me | —CHMe₂ | —CHMe₂ | —CHMe₂ | —CH₂-Me | -Me |
| —(CH₂)₂-Me | —CHMe₂ | —(CH₂)₂-Me | -Me | —(CH₂)₂-Me | -Me |
| —(CH₂)₂-Me | —CHMe₂ | —(CH₂)₂-Me | —CHMe₂ | —(CH₂)₂-Me | -Me |
| —(CH₂)₃-Me | —CHMe₂ | —(CH₂)₃-Me | -Me | —(CH₂)₃-Me | -Me |
| —(CH₂)₃-Me | —CHMe₂ | —(CH₂)₃-Me | —CHMe₂ | —(CH₂)₃-Me | -Me |
| —CH₂—CH=CH₂ | —CHMe₂ | —CH₂—CH=CH₂ | -Me | —CH₂—CH=CH₂ | -Me |
| —CH₂—CH=CH₂ | —CHMe₂ | —CH₂—CH=CH₂ | —CHMe₂ | —CH₂—CH=CH₂ | -Me |
| -Me | -Me | —CHMeCH₂Me | -Me | —CH₂-Me | -Me |
| -Me | -Me | —CHMeCH₂Me | -Me | —(CH₂)₃-Me | -Me |

Me = methyl; Phe = phenyl

Another depsipeptide that may be mentioned is the compound PF 1022 known from EP-A 382 173, of the formula (IIa) below:

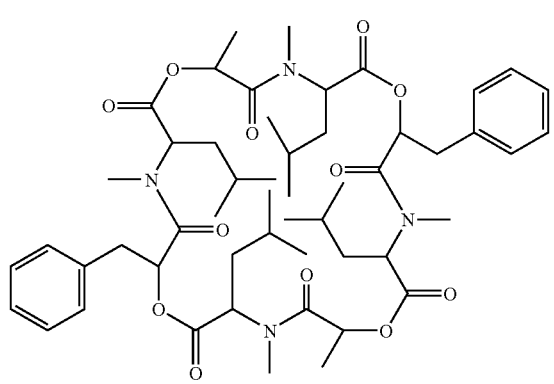

(IIa)

Depsipeptides which may also be mentioned are the compounds known from the PCT application WO 93/19053.

From WO 93/19053, particular mention may be made of the compounds of the formula (IIb) below:

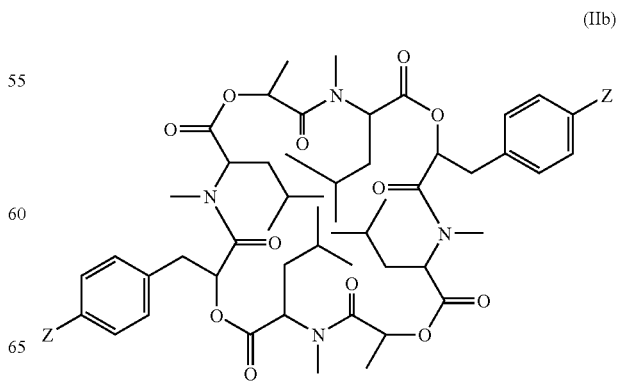

(IIb)

in which

Z represents N-morpholinyl, amino, mono- or dimethylamino.

Moreover, mention may be made of the compounds of the formula (IIc) below:

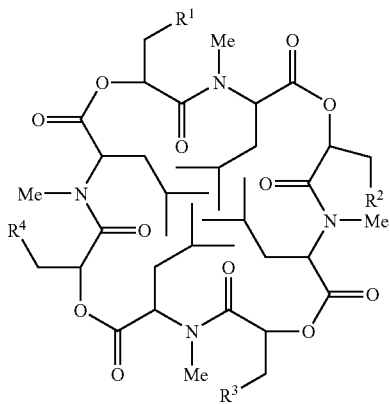

(IIc)

in which $R^1, R^2, R^3, R^4$ independently of one another represent hydrogen, $C_1$-$C_{10}$-alkyl or aryl, in particular phenyl, which are optionally substituted by hydroxyl, $C_1$-$C_{10}$-alkoxy or halogen.

The compounds of the general formula (I) are known and can be obtained by the processes described in EP-A-382 173, DE-A 4 317 432, DE-A 4 317 457, DE-A 4 317 458, EP-A 634 408, EP-A-718 293, EP-A-872 481, EP-A-685 469, EP-A-626 375, EP-A-664 297, EP-A 669 343, EP-A-787 141, EP-A-865 498, EP-A-903 347.

The cyclic depsipeptides having 24 ring atoms also include compounds of the general formula (IId)

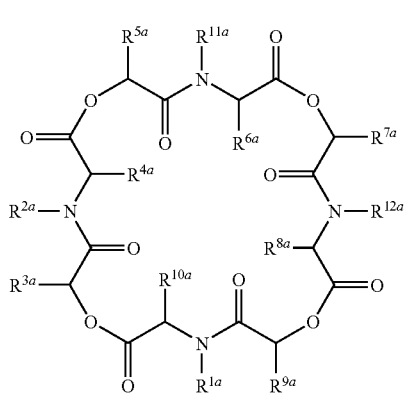

(IId)

in which $R^{1a}, R^{2a}, R^{11a}$ and $R^{12a}$ independently of one another represent $C_{1-8}$-alkyl, $C_{1-8}$-haloalkyl, $C_{3-6}$-cycloalkyl, aralkyl, aryl, $R^{3a}, R^{5a}, R^{7a}, R^{9a}$ independently of one another represent hydrogen or straight-chain or branched $C_{1-8}$-alkyl which may optionally be substituted by hydroxyl, $C_{1-4}$-alkoxy, carboxyl,

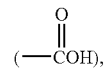

carboxamide,

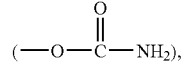

imidazolyl, indolyl, guanidino, —SH or $C_{1-4}$-alkylthio, and furthermore represent aryl or aralkyl which may be substituted by halogen, hydroxyl, $C_{1-4}$-alkyl, $C_{1-4}$-alkoxy, $R^{4a}, R^{6a}, R^{8a}, R^{10a}$ independently of one another represent hydrogen, straight-chain $C_{1-5}$-alkyl, $C_{2-6}$-alkenyl, $C_{3-7}$-cycloalkyl, which may optionally be substituted by hydroxyl, $C_{1-4}$-alkoxy, carboxyl, carboxamide, imidazolyl, indolyl, guanidino, SH or $C_{1-4}$-alkylthio, and also represent aryl or aralkyl which may be substituted by halogen, hydroxyl, $C_{1-4}$-alkyl, $C_{1-4}$-alkoxy, and their optical isomers and racemates.

Preference is given to using compounds of the formula (IId) in which $R^{1a}, R^{2a}, R^{11a}$ and $R^{12a}$ independently of one another represent methyl, ethyl, propyl, isopropyl, n-, s-, t-butyl or phenyl, which is optionally substituted by halogen, $C_{1-4}$-alkyl, OH, $C_{1-4}$-alkoxy, and also represent benzyl or phenylethyl which may optionally be substituted by radicals mentioned under phenyl;

$R^{3a}$ to $R^{10a}$ are as defined above.

Particular preference is given to compounds of the formula (IId) in which $R^{1a}, R^{2a}, R^{11a}$ and $R^{12a}$ independently of one another represent methyl, ethyl, propyl, isopropyl or n-, s-, t-butyl, $R^{3a}, R^{5a}, R^{7a}, R^{9a}$ represent hydrogen, straight-chain or branched $C_{1-8}$-alkyl, in particular methyl, ethyl, propyl, i-propyl, n-, s-, t-butyl which may optionally be substituted by $C_{1-4}$-alkoxy, in particular methoxy, ethoxy, imidazolyl, indolyl or $C_{1-4}$-alkylthio, in particular methylthio, ethylthio, furthermore represent phenyl, benzyl or phenylethyl which may optionally be substituted by halogen, in particular chlorine.

$R^{4a}, R^{6a}, R^{8a}, R^{10a}$ independently of one another represent hydrogen, methyl, ethyl, n-propyl, n-butyl, vinyl, cyclohexyl which may optionally be substituted by methoxy, ethoxy, imidazolyl, indolyl, methylthio, ethylthio, and also represent isopropyl, s-butyl, furthermore represent optionally halogen-substituted phenyl, benzyl or phenylethyl.

The compounds of the formula (IId) can also be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A464 297, EP-A-669 343, EP-A-787 141, EP-A-865 498, EP-A-903 347.

Depsipeptides which are very particularly preferred according to the invention are PF 1022 A (see formula (IIa) and emodepside (PF 1022-221, compound of the formula (IIb) in which both radicals Z represent the morpholinyl radical)). The INN emodepside represents the compound having the systematic name: cyclo[(R)-lactoyl-N-methyl-L-leucyl- (R)-3-(morpholinophenyl)lactoyl-N-methyl-L-leucyl-(R)-lactoyl-N-methyl-L-leucyl-(R)-3-(morpholinophenyl)lactoyl-N-methyl-L-leucyl.

Praziquantel has been known for a long time as a compound active against endoparasites (cf., for example U.S. Pat. No. 4,001,411); corresponding products are commercially available and sold, for example, under the trademark DRONCIT®.

The compositions according to the invention may contain one or more of the above-mentioned cyclic depsipeptides or praziquantel as active compounds. However, preference is given to the combination, i.e. a composition, which comprises both a cyclic depsipeptide and praziquantel, in particular, emodepside and praziquantel.

The particular advantages of the compositions according to the invention are to a considerable extent due to the penetration enhancers specifically selected for this purpose. Penetration enhancers are compounds which improve the topical transdermal application of pharmaceutically active compounds. Numerous different compounds and compound classes have been described in the literature as penetration enhancers. However, it has been found that these give very different results, depending on the active compounds and other auxiliary compounds used. In some cases, there is insufficient transport across the skin, or there are problems with skin-friendliness.

The tests carried out with praziquantel and/or the cyclic depsipeptides showed that, using numerous penetration enhancers described in the literature, it is not possible to obtain results suitable for practical application, whereas the compositions according to the invention, especially owing to the specifically selected penetration enhancers, give excellent results.

Terpene penetration enhancers are described in chapter 6 of "Dermatopharmazie" (Wissenschaftliche Verlagsgesellschaft mbH Stuttgart 2001). Typical groups of terpene penetration enhancers are the terpene hydrocarbons, such as, for example, limonene, .alpha.-pinene or .beta.-carene; terpene alcohols, such as, for example, .alpha.-terpineol, terpine-4-ol or carveol; terpene ketones, such as, for example, carvone, pulegone, piperitone or menthone, and the terpene oxides, such as, for example, limonene oxide, .alpha.-pinene oxide, 1,8-cineol and the related compounds cyclohexene oxide or cyclopentene oxide. Among these, preference is given to the terpene hydrocarbons, in particular to limonene. The terpene penetration enhancers which can be used generally have a skeleton of 10 carbon atoms.

The terpene penetration enhancer is usually employed in amounts of up to 25% by weight, preferably from 2 to 20% by weight, in particular from 5 to 15% by weight.

Suitable penetration enhancers are furthermore also aliphatic fatty acids; these are described, for example, in chapter 6 of "Dermatopharmazie" (Wissenschaftliche Verlagsgesellschaft mbH Stuttgart 2001). These compounds usually have 5 to 18 carbon atoms. Particularly advantageous are furthermore liquid fatty acids, for example those having one or two double bonds. Saturated fatty acids which may be mentioned are, for example, valeric acid, caproic acid, caprylic acid, capric acid, lauric acid, myristic acid, stearic acid, pelargonic acid, isovaleric acid, neopentanoic acid, neoheptanoic acid, neononanoic acid, neodecanoic acid and isostearic acid. Unsaturated fatty acids which may be mentioned are oleic acid, linoleic acid and linolenic acid. Particular preference is given to linoleic acid and especially oleic acid.

Suitable penetration enhancers for the compositions according to the invention are, in addition to the aliphatic fatty acids, aliphatic fatty alcohols; these, too, are described, for example, in chapter 6 of "Dermatopharmazie" (Wissenschaftliche Verlagsgesellschaft mbH Stuttgart 2001). Suitable aliphatic fatty alcohols preferably have 8 to 18 carbon atoms. Examples which may be mentioned are caprylic alcohol, decyl alcohol, lauryl alcohol, 2-lauryl alcohol, myristyl alcohol, cetyl alcohol, stearyl alcohol, isostearyl alcohol, oleoyl alcohol, linolyl alcohol and linolenyl alcohol. Particular preference is given to isostearyl alcohol.

The aliphatic fatty acids and the aliphatic fatty alcohols are usually employed in amounts of up to 25% by weight, preferably from 1 to 20% by weight, particularly preferably from 2 to 15% by weight.

It is possible to employ, as penetration enhancer in the compositions according to the invention, a terpene penetration enhancer or an aliphatic fatty acid acting as penetration enhancer or an aliphatic fatty alcohol acting as penetration enhancer. It is also possible to use combinations of these types of penetration enhancers.

Preference is given to the combined use of a terpene penetration enhancer and an aliphatic fatty acid or an aliphatic fatty alcohol, which results in a surprising synergistic enhancement of activity. Very particular preference is given to the combination of limonene and oleic acid.

Unless indicated otherwise, the stated percentages of the amounts of the individual components of the compositions according to the invention are per cent by weight, based on the total weight of the finished composition.

In the compositions according to the invention, the active compounds should be present in relatively high concentrations, firstly to improve the transdermal action—for example in the case of dose-driving worms, such as *Trichuris vulpis*—and, secondly, to keep the volume to be applied small. However, with such highly concentrated compositions, there is the risk, in the case of topical application (for example spot-on), that the active compound crystallizes on the coat or the skin, which is generally unwanted and, as a rule, worsens skin penetration. Surprisingly, it has been found that by adding aliphatic fatty acids, the crystallization of the active compounds is prevented, the formulation thus being available for a longer period of time for transdermal absorption.

The compositions according to the invention, having favourable homeotherm toxicity, are suitable for controlling pathogenic endoparasites encountered in humans and in animal husbandry and livestock breeding, in productive livestock, breeding stock, zoo animals, laboratory animals, animals used in testing, and pets. They are active against resistant and normally sensitive species and against all or some stages of developments of the pests. By controlling the pathogenic endoparasites, it is intended to reduce disease, mortality and decreasing performance (for example in the production of meat, milk, wool, hides, eggs, honey, etc), so that more economical and simpler animal keeping is possible by using the active compounds. The-pathogenic endoparasites include cestodes, trematodes, nematodes and acantocephales:

Praziquantel controls especially the following endoparasites:

from the order of the *Pseudophyllidea*, for example: *Diphyllobothrium* spp., *Spirometra* spp., *Schistocephalus* spp., *Ligula* spp., *Bothridium* spp., *Diphlogonoporus* spp.

from the order of the *Cyclophyllidea*, for example: *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

from the subclass of the *Monogenea*, for example: *Gyrodactylus* spp., *Dactylogyrus* spp., *Polystoma* spp.

from the subclass of the *Digenea*, for example: *Diplostomum* spp., *Posthodiplostomum* spp., *Schistosoma* spp., *Trichobilharzia* spp., *Omithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp, *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Cyclic depsipeptides control especially the following endoparasites:

from the order of the *Enoplida*, for example: *Trichuris* spp., *Capillaria* spp., *Trichomosoides* spp., *Trichinella* spp.

from the order of the *Rhabditia*, for example: *Micronrema* spp., *Strongyloides* spp. from the order of the *Strongylida*, for example: *Stronylus* spp., *Triodontophorus* spp., *Oesopbagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp.,

*Globocephalus*. spp., *Syngamus* spp., *Cyathostoma* spp., *Metastrongylus* spp., *Dictyocaulus* spp., *Muellerius* spp., *protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

from the order of the *Oxyurida*, for example: *Oxyuris* spp., *Enterobius* spp., *Passalurus* spp., *Syphacia* spp., *Aspiculuris* spp., *Heterakis* spp.

from the order of the *Ascaridia*, for example: *Ascaris* spp., *Toxascaris* spp., *Toxocara* spp., *Parascaris* spp., *Anisakis* spp., *Ascaridia* spp.

from the order of the *Spinruida*, for example: *Gnathostoma* spp., *Physaloptera* spp., *Thelazia* spp., *Gongylonema* spp., *Habronema* spp., *Parabronema* spp., *Draschia* spp., *Dracunculus* spp.

from the order of the *Filariida*, for example: *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

from the order of the *Gigantorbynchida*, for example: *Filicollis* spp., *Moniliformis* spp., *Macracanthorhynchus* spp., *Prosthenorchis* spp.

Using suitable combinations of active compounds, it is possible to cover the entire spectrum of the endoparasites listed above.

The livestock and breeding stock include mammals, such as, for example, cattle, horses, sheep, pigs, goats, camels, water buffalo, donkeys, rabbits, fallow deer, reindeer, fur-bearing animals, such as, for example, mink, chinchilla or racoon, birds, such as, for example, chicken, geese, turkeys, ducks, ostriches.

The laboratory and test animals include mice, rats, guinea pigs, golden hamsters, dogs and cats. The pets include dogs and cats.

Administration can be both prophylactic and therapeutic. Very particular preference is given to the administration to dogs.

Pyrrolidone solvents are pharmaceutically acceptable solvents derived from pyrrolidone. They are preferably pyrrolidones having one or more alkyl substituents of up to 4 carbon atoms. With particular preference, the pyrrolidone solvent is a 2-pyrrolidone which optionally carries an alkyl substituent having 1 to 4 carbon atoms at the ring nitrogen and optionally carries a further alkyl substituent having 1 to 4 carbon atoms at a further ring position. Examples are 1,5-diethyl-2-pyrrolidone, N-ethyl-2-pyrrolidone. Especially preferred are 2-pyrrolidones which optionally carry only one alkyl substituent at the nitrogen, for example 2-pyrrolidone and in particular N-methylpyrrolidone.

The compositions according to the invention comprise the pyrrolidone solvent or mixtures thereof usually in amounts of from 99% by weight to 20% by weight, preferably from 96% by weight to 35% by weight, particularly preferably from 90% by weight to 65% by weight.

In particular for compositions comprising cyclic depsipeptides, the use of a customary antioxidant, such as, for example, BHA, BHT or propyl gallate, is advantageous.

The compositions according to the invention may additionally comprise synergists or further active compounds, for example active compounds acting against pathogenic endoparasites. Such active compounds are, for example, L-2, 3,5,6-tetrahydro-6-phenylimidazothiazole, benzimidazole carbamates, such as febantel, further pyrantel, epsiprantel, or macrocyclic lactones, such as, for example, avermectin, ivermectin or selamectin.

Ready-to-use preparations generally comprise the active compounds in concentrations of in each case 0.01-25% by weight, preferably of 0.1-20 per cent by weight The cyclic depsipeptides are usually employed in amounts of from 0.1 to 8% by weight, preferably from 1 to 6% by weight.

Praziquantel is usually employed in amounts of from 1 to 25% by weight, preferably 5 to 15% by weight, particularly preferably 6 to 14% by weight The compositions are prepared by mixing the appropriate amounts of the components in suitable apparatus. Preferably, the liquid components are mixed, followed by addition of the solid components and preparation of a homogeneous solution.

In general, it has been found to be advantageous to administer amounts of the mixture according to the invention of about 1 to about 100 mg of active compound per kg of body weight per day to obtain effective results. Preference is given to 1 to 10 mg of active compound per kg of body weight The examples below illustrate the invention without limiting it.

EXAMPLES

To prepare the formulations below, the liquid components were initially mixed, and the solid components were then dissolved in the mixture with stirring. All percentages are per cent by weight, based on the total weight of the finished formulation.

Example 1

| | |
|---|---|
| 4% | PF 1022 |
| 8% | praziquantel |
| 79.1% | N-methylpyrrolidone |
| 4.4% | limonene |
| 4.4% | oleic acid |
| 0.1% | BHA |

Example 2

| | |
|---|---|
| 4% | emodepside |
| 8% | praziquantel |
| 79.1% | N-methylpyrrolidone |
| 4.4% | limonene |
| 4.4% | oleic acid |
| 0.1% | BHA |

Example 3

| | |
|---|---|
| 7% | emodepside |
| 14% | praziquantel |
| 68.9% | N-methylpyrrolidone |
| 5% | limonene |
| 5% | oleic acid |
| 0.1% | BHA |

Example 4

| | |
|---|---|
| 4% | emodepside |
| 8% | praziquantel |
| 72.9% | N-methylpyrrolidone |
| 5% | limonene |
| 5% | oleic acid |
| 5% | isostearyl alcohol |
| 0.1% | BHA |

Example 5

| | |
|---|---|
| 4% | emodepside |
| 8% | praziquantel |
| 67.9% | N-methylpyrrolidone |
| 5% | limonene |
| 5% | oleic acid |
| 10% | isostearyl alcohol |
| 0.1% | BHA |

Example 6

| | |
|---|---|
| 4% | emodepside |
| 8% | praziquantel |
| 77.9% | N-methylpyrrolidone |
| 10% | isostearyl alcohol |
| 0.1% | BHA |

Example 7

| | |
|---|---|
| 4% | emodepside |
| 8% | praziquantel |
| 67.9% | N-methylpyrrolidone |
| 20% | isostearyl alcohol |
| 0.1% | BHA |

Example 8

| | |
|---|---|
| 8% | praziquantel |
| 87% | N-methylpyrrolidone |
| 5% | oleic acid |

Example 9

| | |
|---|---|
| 4% | emodepside |
| 8% | praziquantel |
| 70.9% | N-methylpyrrolidone |
| 5% | limonene |
| 4.4% | oleic acid |
| 6.5% | isostearyl alcohol |
| 1.5% | caprylic acid |
| 0.1% | BHA |

Example 10

| | |
|---|---|
| 8% | praziquantel |
| 87% | N-methylpyrrolidone |
| 5% | limonene |

Example 11

| | |
|---|---|
| 8% | praziquantel |
| 83% | N-methylpyrrolidone |
| 4% | limonene |
| 4% | oleic acid |

Example 12

| | |
|---|---|
| 4% | emodepside |
| 8% | praziquantel |
| 72.9% | N-methylpyrrolidone |
| 15% | limonene |
| 0.1% | BHA |

Example 13

| | |
|---|---|
| 8% | praziquantel |
| 77% | N-methylpyrrolidone |
| 15% | limonene |

Example 14

| | |
|---|---|
| 8% | praziquantel |
| 72% | N-methylpyrrolidone |
| 20% | limonene |

Example 15

| | |
|---|---|
| 4% | emodepside |
| 8% | praziquantel |
| 67.9% | N-methylpyrrolidone |
| 20% | limonene |
| 0.1% | BHA |

Example 16

| | |
|---|---|
| 8% | praziquantel |
| 78% | N-methylpyrrolidone |
| 4.4% | limonene |
| 4.4% | oleic acid |
| 5% | isostearyl alcohol |

Example 17

| | |
|---|---|
| 4% | emodepside |
| 8% | praziquantel |
| 72.9% | N-methylpyrrolidone |
| 5% | limonene |
| 5% | linoleic acid |
| 5% | isostearyl alcohol |
| 0.1% | BHA |

Example 18

| | |
|---|---|
| 6% | emodepside |
| 12% | praziquantel |
| 71.9% | N-methylpyrrolidone |
| 5% | limonene |
| 5% | oleic acid |
| 0.1% | BHA |

Biological Example

The solutions of Example 2 or 3 were applied to the coat on the back of the parasite-infected animals. Details can be seen from the table below:

| Formulation | Animal | Parasite | Number of treated animals | Dose (per kg of body weight) | Effect against nematodes/cestodes |
|---|---|---|---|---|---|
| Ex. 2 | Dogs | *Ancylostoma caninum* | 6 | 12 mg emodepside 24 mg praziquantel | 100% |
| | | *U. stenocephala* | 6 | | 100% |
| | | *T. vulpis* | 6 | | 90% |
| | | *T. canis* | 6 | | 100% |
| | | *Taenia* sp. | 6 | | 100% |
| Ex. 3 | Dogs | *D. caninum* | 6 | 24 mg praziquantel | 98% |
| | | *T. vulpis* | 6 | 12 mg emodepside | 100% |

The invention claimed is:

1. A composition for controlling endoparasites on dogs comprising:
   emodepside and praziquantel;
   a pyrrolidone solvent; and,
   a terpene penetration enhancer, wherein the terpene penetration enhancer is limonene.

2. The composition according to claim 1, further comprising an aliphatic fatty acid acting as penetration enhancer.

3. The composition according to claim 2, wherein the aliphatic fatty acid is linoleic acid.

4. The composition according to claim 2, wherein the aliphatic fatty acid is oleic acid.

5. The composition according to claim 1, further comprising an aliphatic fatty alcohol acting as penetration enhancer.

* * * * *